(12) United States Patent
Cai et al.

(10) Patent No.: US 9,534,026 B2
(45) Date of Patent: Jan. 3, 2017

(54) CORN ACTIVE PEPTIDE ADDITIVE FOR CELL CULTURE MEDIUM

(71) Applicant: CHINA NATIONAL RESEARCH INSTITUTE OF FOOD AND FERMENTATION INDUSTRIES, Beijing (CN)

(72) Inventors: Muyi Cai, Beijing (CN); Feng Lin, Beijing (CN); Yan Liu, Beijing (CN); Haixin Zhang, Beijing (CN); Ruizeng Gu, Beijing (CN); Jun Lu, Beijing (CN); Ying Wei, Beijing (CN)

(73) Assignee: CHINA NATIONAL RESEARCH INSTITUTE OF FOOD & FERMENTATION INDUSTRIES, Beijing (CN)

(*) Notice: Subject to any disclaimer, the term of this patent is extended or adjusted under 35 U.S.C. 154(b) by 0 days.

(21) Appl. No.: 14/583,058

(22) Filed: Dec. 24, 2014

(65) Prior Publication Data
US 2015/0118709 A1 Apr. 30, 2015

Related U.S. Application Data

(63) Continuation of application No. PCT/CN2014/071394, filed on Jan. 24, 2014.

(30) Foreign Application Priority Data

Oct. 31, 2013 (CN) .......................... 2013 1 0533664

(51) Int. Cl.
C12N 5/00 (2006.01)
C07K 14/415 (2006.01)
C12P 21/06 (2006.01)

(52) U.S. Cl.
CPC ........... *C07K 14/415* (2013.01); *C12N 5/0043* (2013.01); *C12P 21/06* (2013.01); *C12Y 304/00* (2013.01); *C12N 2500/76* (2013.01); *Y02P 20/52* (2015.11)

(58) Field of Classification Search
None
See application file for complete search history.

(56) References Cited

FOREIGN PATENT DOCUMENTS

| CN | 1786183 A | 6/2006 | |
|---|---|---|---|
| CN | 102892878 A | 1/2013 | |
| CN | 102911992 A | 2/2013 | |
| CN | 103305576 A | 9/2013 | |
| JP | S62-65698 A | 3/1987 | |
| JP | H02-295437 A | 12/1990 | |
| JP | H03-204900 A | 9/1991 | |
| JP | 04-16139 A | 1/1992 | |
| JP | H06-153931 A | 6/1994 | |
| JP | 2000-279126 A | 10/2000 | |
| JP | 2011-521629 A | 7/2011 | |
| WO | WO 2011/133902 | * 10/2011 | ............... C07K 5/06 |
| WO | WO 2012/155295 A1 | 11/2012 | |

OTHER PUBLICATIONS

Cheung et al., The Journal of Biological Chemistry (1980) 255(2), 401-407.*
Parris et al., J. Agric. Food Chem. (2008) 56, 2620-2623.*
Petsch et al., Journal of Biotechnology (2000) 76, 97-119.*
Ruizeng Gu et al., "Application and Research Progress of Protein Hydrolysates in Animal Cell Culture" Biotechnology Bulletin, vol. 9, 2012, pp. 21-27 (Abstract).
Chinese International Search Report of corresponding International PCT Application No. PCT/CN2014/071394, dated Aug. 6, 2014.
The Japanese Examination Report of corresponding Japan patent application No. 2015-544345 dated Feb. 16, 2016.

* cited by examiner

*Primary Examiner* — Marcela M Cordero Garcia
*Assistant Examiner* — Catherine Mader
(74) *Attorney, Agent, or Firm* — J.C. Patents (57) ABSTRACT

The present invention provides a corn active peptide additive for cell culture medium, wherein in the corn active peptide additive, oligopeptides with molecular weight of lower than 1000 Dalton account for equal to or more than 90 wt % of total proteins, and the oligopeptides at least comprise one or more of AP, SAP, PAL, VNAP, PSSQ, and TQPGPQ. The corn active peptide additive of the present invention can be compounded with various basic culture mediums for serum-free culture of various animal cells, which not only substantially lowers the cost for cell culturing and reduces pollution and other problems caused by an animal derived component, but also can promote cell proliferation, improve cell viability and enhance expression of cell products.

10 Claims, 6 Drawing Sheets

CORN ACTIVE PEPTIDE ADDITIVE FOR CELL CULTURE MEDIUM

CROSS REFERENCE TO RELATED APPLICATIONS

This application is a continuation of International Application No. PCT/CN2014/071394, filed on Jan. 24, 2014, which claims priority to China Patent Application No. 201310533664.X filed with the Chinese Patent Office on Oct. 31, 2013, entitled "CORN ACTIVE PEPTIDE ADDITIVE FOR CELL CULTURE MEDIUM". The contents of the above identified applications are incorporated herein by reference in their entireties.

TECHNICAL FIELD

The present invention relates to a cell culture medium additive, and in particular to a corn active peptide additive for cell culture medium.

BACKGROUND

A culture medium is the most direct and important environmental factor for determining growth and metabolism of cultured cells in vitro. Animal cell culture medium typically contains additives derived from animals, such as serum. However, with global fulminant epidemic of mad cow disease, use of animal derived additives, such as serum, brings transmissible spongiform encephalopathy (TSE) virus and other dangerous substances in biopharmacy industry, sharply increasing security risk for the biopharmacy industry. Drug regulators all over the world require drug makers to reduce the use of bovine derived constituents during pharmaceutical production, and relevant legislatures are increasingly opposing the use of animal derived constituents such as bovine serum in pharmaceutical field. Use of animal derived constituents in commercial production of culture medium is strictly controlled by the United States Food and Drug Administration (FDA) and the European Medicines Agency (EMA) to ensure medication safety of a patient. Meanwhile, serum and other animal derived culture medium additives contain macromolecular proteins such as growth factor, transport protein, anchoring factor and hormone, which will affect post-separation and purification of biological products such as antibody-medicine and vaccine, and eventually affect yield of the product obtained, increasing cost of production. Therefore, development and application of non-animal derived cell culture medium additives accords with current developing direction, and has become an important subject in culture of animal cells in vitro and biopharmacy fields.

Corn gluten meal can be obtained by wet-milling corn to obtain crude starch milk, separating protein from the crude starch milk to obtain gluten water, and then concentrating and desiccating the gluten water. The corn gluten meal is a major by-product during wet-milling process of corn to produce starch, which contains more than 60% of protein, and inorganic salts and a variety of vitamins. Corn active peptide is a mixture of small molecular peptides obtained from the corn gluten meal as a raw material by pretreatment, enzymatic hydrolysis, multi-stage separation and purification, concentration and desiccation and other processes. Corn active peptide is a sophisticated product in the field of bio-processing and conversion utilization of natural corn protein resources. The corn active peptide is derived from plant protein, and thus the problem that animal derived constituent such as serum is potentially polluted by virus microorganism can be avoided; quality thereof is consistent between batches, which is advantageous to improve producing stability of cell products; the corn active peptide contains no macromolecular protein, which is beneficial to downstream separation and purification of the cell products.

The corn active peptide is rich in nutrient substances, and easy to be polluted by bacteria microorganism during processing and storing, thus producing a large amount of bacterial endotoxin. It will change cell morphology, damage cell membrane structures and induce cell apoptosis, etc., when used as a cell culturing additive, which is disadvantageous to growth of the cell cultured in vitro. In addition, different processes have great influence on composition of the obtained corn active peptide product, while constituents of animal serum are complex wherein many constituents are unknown up to now, therefore, it cannot be determined that whether existence or absence of one or some constituents will adversely affect cell growth, which accordingly brings difficulties to application of the corn active peptide as a serum-free culture medium additive.

SUMMARY

The present invention provides a corn active peptide additive and its application, the corn active peptide has a low endotoxin content, and when used as a cell culture medium additive, it can compound with various basic culture mediums for serum-free culturing various cell lines, thus promoting cell proliferation, improving cell viability and enhancing expression of cell products.

The present invention also provides a method of preparing the corn active peptide for cell culture medium. The method is easy to operate and has high enzymolysis efficiency, and the method can efficiently separate small molecule active peptide from large molecule protein, bacterial endotoxin and small molecule salt, and thus is suitable for a large-scale industrial production.

The present invention provides a corn active peptide additive for cell culture medium, wherein oligopeptides with molecular weight of lower than 1000 Dalton account for equal to or more than 90 wt % of total proteins, and the oligopeptides at least comprise one or more of AP, SAP, PAL, VNAP, PSSQ, and TQPGPQ.

Further, the oligopeptide also comprises one or more of AY, NAP, PVIN, and AYPQ.

Further, the endotoxin content in the corn active peptide additive is less than 200 EU/g, in particular less than 50 EU/g.

The corn active peptide additive according to the present invention is obtained by performing enzymolysis on the corn gluten meal using a non-specific protease and a specific protease in sequence and then performing separation and purification.

The non-specific protease in the present invention refers to a protease having lower specificity to the substrate on which it acted and broader substrate specificity, such as alkaline protease which can hydrolyze peptide chains of various protein molecules to obtain polypeptide or amino acid, and bromelain which can decompose various proteins, peptides, esters, amides, etc. The specific protease in the present invention refers to a protease having relatively strict substrate specificity and only acting on some certain peptide bonds in the protein molecules, such as the peptide bond formed by carboxypeptidase catalytically hydrolyzing the terminal amino acid containing carboxyl.

In a specific embodiment of the present invention, the non-specific protease is selected from one or more of papain, alkaline protease, neutral protease and bromelain, and the specific protease is selected from one or two of carboxypeptidase and flavourzyme; specifically, the non-specific protease is selected from two or more of papain, alkaline protease, neutral protease and bromelain. In the present invention, a specific protease is firstly used to perform enzymolysis to the corn gluten meal, and then a non-specific protease is used to perform further enzymolysis to the resulting hydrolysate. When using these two proteases together, a higher enzymolysis efficiency can be reached, and contents of active peptides, specially active peptides with small molecular weight in the enzymatic hydrolysate can reach to a higher level.

Further, the non-specific protease has an enzyme level of 2000-6000 units per gram of protein, including two or more of papain with 0-1000 units, alkaline protease with 500-2000 units, neutral protease with 500-2000 units and bromelain with 0-1500 units; and the specific protease has an enzyme level of 2000-3000 units per gram of protein, including one or two of carboxypeptidase with 500-2000 units and flavourzyme with 1000-2000 units. In the present invention, enzyme activity unit of each protease is defined as: under experimental conditions, the enzyme level used to produce 1 g of tyrosine per minute by hydrolyzing casein is defined as one enzyme activity unit, and the protein in the per gram of protein is specifically refers to the protein in the corn gluten meal, that is, added units of each protease corresponds to 1 gram of protein contained in the corn gluten meal.

Performing enzymolysis on the corn gluten meal using the non-specific protease and specific protease provided in the present invention can produce various oligopeptides with molecular weight of lower than 1000 Dalton. A person skilled in the art can separate and purify the oligopeptides from the resulting enzymatic hydrolysate using conventional means in prior art, such as centrifugation, microfiltration, ultrafiltration, etc. In a specific embodiment of the present invention, the separation and purification include one or more of centrifugation, microfiltration, cation exchange, nanofiltration and ultrafiltration; particularly, the separation and purification in the present invention are specifically as follows: performing centrifugation, microfiltration, cation exchange, nanofiltration and ultrafiltration in sequence on the enzymatic hydrolysate, wherein the microfiltration is performed by a filter membrane with an aperture of 50-500 nm, the nanofiltration is performed by a filter membrane with molecular weight cut-off of 100-300 Dalton, and the ultrafiltration is performed by a filter membrane with molecular weight cut-off of 5000-13000 Dalton.

The present invention also provides the use of the above corn active peptide additive in cell serum-free culture medium.

Further, the cell is selected from one or more of CHO cell, Vero cell, HEK-293 cell, BHK-21 cell, MARC-145 cell, hybridoma cell, and MDCK cell.

The present invention also provides the use of the above corn active peptide additive in promoting cell proliferation, improving cell viability and/or enhancing expression of cell products.

Further, the cell is selected from one or more of CHO cell, Vero cell, HEK-293 cell, BHK-21 cell, MARC-145 cell, hybridoma cell, and MDCK cell.

The present invention also provides a serum-free culture medium comprising any one of the above corn active peptide additives, wherein the concentration of the corn active peptide additive in the serum-free culture medium is 0.01-20 g/L, such as 1-10 g/L, and further 2-4 g/L.

The present invention also provides a method of preparing any one of the above corn active peptide additives, comprising the following steps:

1) performing a first enzymolysis process on the corn gluten meal using non-specific protease to obtain a first enzymatic hydrolysate; and then performing a second enzymolysis process on the first enzymatic hydrolysate using specific protease to obtain a corn protein enzymatic hydrolysate;

2) performing centrifugation on the corn protein enzymatic hydrolysate, and then performing microfiltration, cation exchange, nanofiltration and ultrafiltration in sequence on centrifugalized supernatant to obtain a corn active peptide; wherein the microfiltration is performed by a filter membrane with an aperture of 50-500 nm, the nanofiltration is performed by a filter membrane with molecular weight cut-off of 100-300 Dalton, and the ultrafiltration is performed by a filter membrane with molecular weight cut-off of 5000-13000 Dalton.

According to the preparing method of the present invention, the non-specific protease has an enzyme level of 2000-6000 units per gram of protein, including two or more of papain with 0-1000 units, alkaline protease with 500-2000 units, neutral protease with 500-2000 units and bromelain with 0-1500 units; and the specific protease has an enzyme level of 2000-3000 units per gram of protein, including one or two of carboxypeptidase with 500-2000 units and flavourzyme with 1000-2000 units. A person skilled in the art can adjust conditions, such as enzymolysis temperature and pH value, of the first enzymolysis process and the second enzymolysis process according to the composition of the enzyme used.

Further, the step 1) specifically comprises: mixing the corn gluten meal with water to obtain a protein solution, and then adding the non-specific protease into the protein solution to reach an enzyme level of 2000-6000 units per gram of protein, and performing the first enzymolysis process at 40-60° C. for 1.5-4.5 hours, to obtain the first enzymatic hydrolysate; and then adding the specific protease into the first enzymatic hydrolysate to reach an enzyme level of 2000-3000 units per gram of protein, performing the second enzymolysis process at 40-60° C. for 2-3 hours, and then inactivating enzyme to obtain the corn protein enzymatic hydrolysate. The inactivating enzyme specifically can conduct as follows: heating the enzymatic hydrolysate treated by the second enzymolysis process to 85-130° C. and keeping at this temperature for 10-20 minutes.

Further, before performing the first enzymolysis process, the method further comprises: heating the protein solution to 90-95° C. and keeping at this temperature for 15-60 min to denature the protein in the protein solution, which is beneficial for the following enzymolysis process.

According to the preparing method of the present invention, the centrifugation in step 2) has a rotation speed of 4000-12000 r/min, and can be conducted by a disc separator.

According to the preparing method of the present invention, the microfiltration in step 2) specifically comprises: performing a first microfiltration on the centrifugalized supernatant using a filter membrane with an aperture of 200-500 nm to obtain a first microfiltrate, and then performing a second microfiltration on the first microfiltrate using a filter membrane with an aperture of 50-200 nm to obtain a second microfiltrate.

Further, the filter membrane used in the first microfiltration and the second microfiltration is a ceramic membrane;

the operation pressure (transmembrane pressure) is 10-30 psi; the protein contents in the first microfiltrate and the second microfiltrate are 1-5%, the protein content mentioned in the present invention is mass content. If the protein content is too low, the microfiltration time will be increased and the production efficiency will be reduced, and if the protein content is too high, the filter load of the filter membrane will be increased and the service life of the filter membrane will be reduced. After research, the present inventor has found that protein content of 1-5% is suitable. In addition, in the present invention, the filtration is a two-step filtration by a ceramic membrane, i.e., a primary filtration and an in-depth filtration in sequence, the primary filtration is used for removing soluble proteins with big molecule weight which is not removed by centrifugation, and the in-depth filtration is mainly for further purification to remove impurity proteins, etc. The two-steps filtration not only can improve the filtration efficiency, but also has a better filtration effect.

According to the preparing method of the present invention, the cation exchange in step 2) can specifically comprise: packing the cation exchange resin into a chromatographic column, washing the resin with distilled water of 3-5 times the volume of the column, and then introducing the filtrate into the chromatographic column with a linear flow rate of 0.5-3 cm/min, washing the filtrate with distilled water of 2-5 times the volume of the column, and then performing elution using 1M NaCl solution with a linear flow rate of 1-5 cm/min, and collecting the eluent to obtain a purified liquid. Wherein the cation exchange resin can be hydrogen cation exchange resin such as D001 cation exchange resin, and in a specific embodiment of the present invention, D001-FD cation exchange resin is adopted. In the present invention, the above filtrate is further separated and purified by ion exchange, which can further efficiently separate the active peptide in the filtrate from other impurities with weak current, with opposite charges and electrically neutral (such as starch) so as to better insure the purity and quality of the active peptide product.

According to the preparing method of the present invention, the nanofiltration in step 2) specifically comprises: concentrating the centrifugalized supernatant after cation exchange to protein content being 5-10% using a rolled membrane with molecular weight cut-off of 100-300 Dalton, and then washing and filtering to make the washed and filtered centrifugalized supernatant has an inorganic salt content of less than or equal to 5%; and then concentrating the washed and filtered centrifugalized supernatant to protein content being 20-40%. The inventor has found that the effect is poor when performing nanofiltration directly, which may be caused by small aperture of the nanofiltration membrane which is easy to be blocked by the active peptide molecule. Therefore, a step of washing and filtering is added by the inventor when performing nanofiltration, and after research, the inventor has found that a better nanofiltration effect can be obtained when the protein content in the solution is controlled to be 5-10% before washing and filtering.

According to the preparing method of the present invention, the ultrafiltration in step 2) is performed by a rolled membrane with molecular weight cut-off of 5000-13000 Dalton, to further remove the endotoxin in the processed solution, wherein the operation pressure is 10-30 psi.

Further, the preparing method further comprises drying after performing the ultrafiltration, to obtain the corn active peptide with moisture content of 1.5-5%.

The technical solution of the present invention at least has the following advantages:

1. The corn active peptide of the present invention has a higher oligopeptide content and a lower endotoxin content, when used as a cell culture medium additive, it can be flexibly compounded with various basic culture mediums without adding other serum, that is, it can be used for serum-free culture of various animal cells.

2. The preparing method of the present invention is easy to operate and has high enzymolysis efficiency, and a small molecule active peptide in the enzymatic hydrolysate have a higher content, in addition, the preparing method can efficiently separate the small molecule active peptide from a big molecule protein, bacterial endotoxin and small molecule salt, and thus is suitable for a large-scale industrial production.

3. The serum-free culture medium of the present invention can be conveniently formulated and has a low cost, which can be used for culturing various cell lines, and additionally can promote cell proliferation, increase cell viability and enhance expression of cell products.

DETAILED DESCRIPTION

In order to make the object, technical solution and advantages of the present invention more clear, the present invention will be clearly and completely described in conjunction with the accompanying drawings. Apparently, the embodiments described are a part of the embodiments of the present invention, but not all the embodiments. On the basis of the embodiments of the present invention, all the other embodiments obtained by a person skilled in the art without creative work belong to the protection scope of the present invention.

Embodiment 1

1. Enzymolysis Process

Add 12-fold deionized water into a corn gluten meal with protein content of equal to or more than 60%, mix them uniformly and then heat to about 90° C. and keep the temperature for 15-20 minutes, and then lower the temperature to about 55° C. to obtain a protein solution, adjust pH value of the protein solution to 7-8, and add a compound non-specific protease obtained by mixing neutral proteinase NEUTRASE O.D.L (Novozymes company) and alkaline protease ALKALINE PROTEASE CONCENTRATE (DSM company) into the protein solution in an enzyme level of about 4000 units per gram of protein (where both of the neutral proteinase NEUTRASE O.D.L and the alkaline protease ALKALINE PROTEASE CONCENTRATE have an enzyme level of about 2000 units), perform a first enzymolysis process for 2.5 hours while remaining the temperature at about 55° C., to obtain a first enzymatic hydrolysate; adjust pH value of the first enzymatic hydrolysate to 7.5-8.5, and then add carboxypeptidase ACCEL-ERZYME CPG (DSM company) into the first enzymatic hydrolysate in an enzyme level of about 2000 units per gram of protein, perform a second enzymolysis process for 2.5 hours while remaining the temperature at about 50° C., and then heat the resulting enzymatic hydrolysate to 110-120° C. and keep the temperature for 15-20 minutes for enzyme deactivation, to obtain a corn protein enzymatic hydrolysate.

2. Microfiltration

Put the corn protein enzymatic hydrolysate into a disc separator and perform centrifugation at a rotation rate of 4000-12000 r/min, to separate the liquid of the corn protein enzymatic hydrolysate from dregs therein, and then collect the centrifugal supernatant for further use.

Perform a first microfiltration (primary filtration) on the centrifugal supernatant using a ceramic membrane with 200-500 nm aperture to obtain a first microfiltration solution, wherein the time of the first microfiltration is controlled to be 1-3 h and the operation pressure is controlled to be 10-30 psi.

Perform a second microfiltration (in-depth filtration) on the first microfiltration solution using a ceramic membrane with 50-200 nm aperture to obtain a second microfiltration solution, wherein the time of the second microfiltration is controlled to be 1-3 h and the operation pressure is controlled to be 10-30 psi.

3. Cation Exchange

Pack the cation exchange resin D001-FD dedicated for food industry into a chromatographic column, wash the resin with distilled water of 3-5 times the volume of the column, and then introduce the second microfiltration solution into the chromatographic column with a linear flow rate of 0.5-3 cm/min, control injection volume of the second microfiltration solution to be 20-100% of the chromatographic column volume, wash it with distilled water to 2-5 times the volume of the column, and then perform elution using 1M NaCl solution with a linear flow rate of 1-5 cm/min, collect the eluent to obtain a purified liquid.

4. Nanofiltration and Ultrafiltration

Concentrate the purified liquid to protein content being 5-10% using a rolled membrane with molecular weight cut-off of 100-300 Dalton, and then add distilled water to perform washing and filtering to reach 3-5 times the primary volume, making inorganic salt content in the washed and filtered purified liquid being less than 5%, and then further perform concentration to protein content being 20-40%, and collect the concentrated solution;

Perform ultrafiltration to the concentrated solution using a rolled membrane with molecular weight cut-off of 5000-13000 Dalton, in order to remove endotoxin in the concentrated solution and obtain a corn active peptide solution with endotoxin content of less than 50 EU/g.

5. Drying Treatment

Perform spray drying on the corn active peptide solution to obtain a faint yellow corn active peptide powder with moisture content of 1.5%-5%, wherein inlet temperature and outlet temperature of the spray drying purified air are controlled to be 120-180° C. and 65-90° C., respectively.

6. Detection

Perform analysis on basic physicochemical composition and molecular weight distribution of each component in the obtained corn active peptide using a conventional method. The results are shown in Table 1 and Table 2, respectively.

Figure 1:
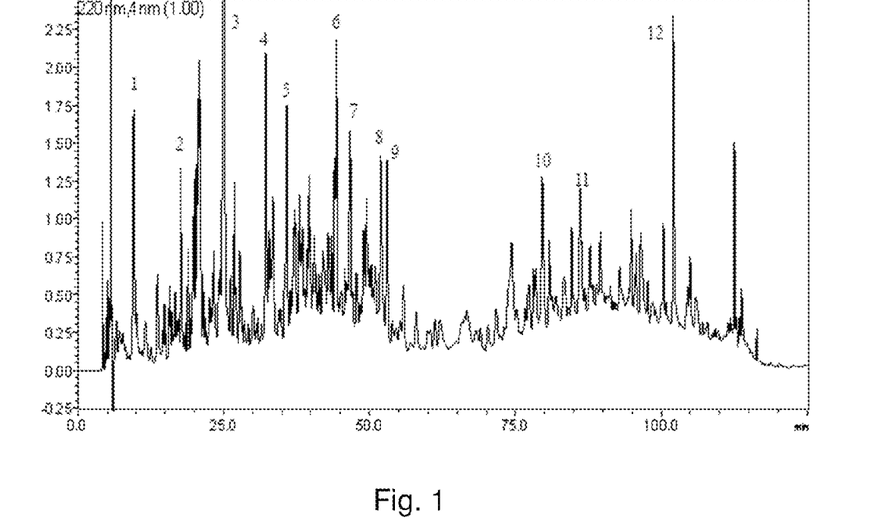
FIG. 1 is a diagram of high performance liquid chromatography of the corn active peptide according to Embodiment 1.

Separate the obtained corn active peptide using RP-HPLC (Shimadzu LC-20A high performance liquid chromatography, SHIMADZU company of Japan), perform primary structure identification on main components using Q-TOF2 mass spectrometer (Micromass company of UK), and specifically:

Take 1 g of the corn active peptide sample obtained above, dilute with mobile phase A to 100 ml, perform ultrasonic oscillation 10 min to make the sample dissolved and mixed sufficiently, and then formulate the dissolved and mixed sample into a corn active peptide solution with a concentration of 0.1 mg/ml, and then inject the solution after being filtered using polytetrafluoroethylene membrane with an aperture of 0.2 μm; wherein chromatographic conditions are as follows: mobile phase A is: V(water):V(trifluoroacetic acid)=100:0.1 ml/min; mobile phase B is: V(acetonitrile):V(water):V(trifluoroacetic acid)=80:20:0.1; detection wavelength: UV220 nm; flow rate: 0.6 mL/min; column temperature: 32° C.; injection volume: 50 μl; FIG. 1 shows a high performance liquid chromatogram of the obtained corn active peptide.

Collect different components corresponding to peaks into different tubes (at least collect components corresponding to peaks with serial numbers 1-12 in FIG. 1), remove the organic solvent using a nitrogen blowing instrument, perform freeze drying to obtain a powder, and then perform mass spectrometric detection, wherein chromatographic conditions are as follows: ionization method: nanoelectrospray positive ion; atomizing gas: N2; collision gas: Ar; source temperature: 80° C.; cone voltage: 50V; TOF accelerating voltage: 9.1 kV; MCP detector voltage: 2150V; capillary voltage: 800V; mass accuracy of MS and MS/MS: 0.1 Da; after obtaining the ESI-MS chromatogram by primary MS scanning, select the ion to be detected from the ESI-MS chromatogram, and then perform ESI-MS/MS analysis, after the chromatogram being converted by the MaxEnt 3 of the mass spectrometer, deduce sequences of peptide fragments by Peptide Sequencing. Primary structures of main components of the corn active peptide are as shown in Table 3.

As can be seen from the results of Table 1 and Table 2: the total protein content in the corn active peptide obtained in the present embodiment can be up to 91% or more, wherein oligopeptides with molecular weight of equal to or lower than 1000 Da account for equal to or more than 98 wt % of total proteins. As can be seen from the results of Table 3 that: the main components of the corn active peptide include: AP, SAP, PAL, VNAP, PSSQ, AY, NAP, etc., and the peptide identified for the first time from the corn active peptide include: AP (molecular weight of 186.21 Da), SAP (molecular weight of 273.29 Da), PAL (molecular weight of 299.37 Da), VNAP (molecular weight of 399.45 Da), PSSQ (molecular weight of 417.19 Da), TQPGPQ (molecular weight of 626.27 Da).

Embodiment 2

This embodiment is conducted as described in Embodiment 1, except that: add 9-fold distilled water into the corn gluten meal having protein content of equal to or greater than 60%, mix them uniformly and then heat them to 90-95° C., keep the temperature for 55-60 minutes, and then lower the temperature to 55-55° C. and adjust pH value of the protein solution to 7-8, add a compound non-specific protease obtained by mixing papain (Nanning Pangbo Biological Engineering Co., Ltd) and bromelain (Nanning Pangbo Biological Engineering Co., Ltd) into the protein solution (wherein the papain and the bromelain have an enzyme level of about 1000 units and about 1500 units, respectively) into the protein solution in an enzyme level of about 2500 units per gram of protein, perform the first enzymolysis process for 1.5 h while remaining the temperature at 50-55° C., to obtain the first enzymatic hydrolysate; adjust the pH value of the first enzymatic hydrolysate to 8-9, and then add a compound specific protease obtained by mixing carboxypeptidase Validase FP Conc. (DSM Company) and flavourzyme FLAVOURZYME 500 MG (Novozyme Company) into the first enzymatic hydrolysate in an enzyme level of about 3000 units per gram of protein (wherein both the carboxypeptidase ACCELERZYME CPG and the flavourzyme FLAVOURZYME 500 MG have an enzyme level of about 1500 units), perform the second enzymolysis process for 3 h while remaining the temperature at 50-55° C., and then heat the enzymatic hydrolysate to 90-100° C. and keep the temperature for 15-20 min for enzyme deactivation, to obtain the corn protein enzymatic hydrolysate. The finally obtained faint yellow corn active peptide powder has a moisture content of 1.5%-5%.

Upon detection, in the corn active peptide obtained in the present embodiment, oligopeptides with molecular weight of lower than 1000 Da account for equal to or more than 95 wt % of total proteins, endotoxin content is less than 50 EU/g. The corn active peptide contains 18 kinds of polypeptides with their primary structures as shown in Table 3. The basic physicochemical composition and molecular weight distribution of each component of the corn active peptide are shown in Table 1 and Table 2.

Embodiment 3

This embodiment is conducted as described in Embodiment 1, except that: add 10-fold distilled water into the corn gluten meal having protein content of equal or greater than 60%, mix them uniformly and then heat them to 95° C., keep the temperature for 35-40 minutes, and then lower the temperature to 45-50° C. and adjust the pH value of the protein solution to 7-8, add a compound non-specific protease obtained by mixing neutral protease Validase BNP-L (DSM Company), alkaline protease Alcalase 2.4 L (Novozyme Company), papain (Nanning Pangbo Biological Engineering Co., Ltd) and bromelain (Nanning Pangbo Biological Engineering Co., Ltd) into the protein solution in an enzyme level of about 6000 units per gram of protein (wherein the neutral protease Validase BNP-L, the alkaline protease Alcalase 2.4 L, the papain and the bromelain have an enzyme level of about 2000 units, about 2000 units, about 1000 units and about 1000 units, respectively), perform the first enzymolysis process for 3 h while remaining the temperature at 45-50° C., to obtain the first enzymatic hydrolysate; adjust pH value of the first enzymatic hydrolysate to about 5.5, and then add flavourzyme MAXZPRO XF (DSM Company) into the first enzymatic hydrolysate in an amount of about 2000 units of enzyme per gram of protein, perform the second enzymolysis process for about 2.5 h while remaining the temperature at about 55° C., and then heat the enzymatic hydrolysate to 120-130° C. and keep the temperature for 10-15 min for enzyme deactivation, to obtain the corn protein enzymatic hydrolysate. The finally obtained faint yellow corn active peptide powder has a moisture content of 1.5%-5%.

Upon detection, in the corn active peptide obtained in the present embodiment, oligopeptides with molecular weight of lower than 1000 Da account for equal to or more than 98 wt % of total proteins, the endotoxin content is less than 50 EU/g. The corn active peptide contains 18 kinds of polypeptides with their primary structures as shown in Table 3. The basic physicochemical composition and molecular weight distribution of each component in the obtained corn active peptide are shown in Table 1 and Table 2.

TABLE 1

The basic physicochemical composition of the corn active peptide of the present invention

| Composition | Embodiment 1 | Embodiment 2 | Embodiment 3 |
|---|---|---|---|
| Total proteins (dry basis, %) | 91.77 ± 0.45 | 92.43 ± 0.34 | 93.21 ± 0.40 |
| Fat (%) | 0.06 ± 0.02 | 0.05 ± 0.01 | 0.04 ± 0.01 |
| Ash content (%) | 3.32 ± 0.28 | 3.25 ± 0.21 | 2.99 ± 0.16 |
| Moisture (%) | 3.95 ± 0.33 | 3.30 ± 0.20 | 2.88 ± 0.16 |

TABLE 2

The molecular weight distribution of the corn active peptide of the present invention

| Range of molecular weight | Embodiment 1 | Embodiment 2 | Embodiment 3 |
|---|---|---|---|
| Equal to or more than 10000 Da (%) | 0.00 | 0.00 | 0.00 |
| 3000-10000 Da (%) | 0.00 | 0.00 | 0.00 |
| 1000-3000 Da (%) | 1.61 ± 0.09 | 4.13 ± 0.12 | 1.29 ± 0.11 |
| 500-1000 Da (%) | 10.87 ± 0.45 | 15.36 ± 0.36 | 9.42 ± 0.41 |
| 140-500 Da (%) | 74.46 ± 0.83 | 68.76 ± 0.73 | 76.96 ± 0.72 |
| Equal to or less than 140 Da (%) | 13.06 ± 0.21 | 11.75 ± 0.22 | 12.33 ± 0.20 |
| Equal to or less than 1000 Da | 98.39 ± 0.80 | 95.87 ± 0.95 | 98.71 ± 0.93 |

TABLE 3

Primary structures of main components of the corn active peptide of the present invention

| Serial number | Sequence | Molecular weight |
|---|---|---|
| 1 | AP | 186.21 |
| 2 | AY | 252.12 |
| 3 | SAP | 273.29 |
| 4 | PAL | 299.37 |
| 5 | NAP | 300.31 |
| 6 | VNAP | 399.45 |
| 7 | PSSQ | 417.19 |
| 8 | PVIN | 441.53 |
| 9 | AYPQ | 477.21 |
| 10 | TQPGPQ | 626.27 |
| 11 | PPY | 375.42 |
| 12 | IP | 228.29 |
| 13 | LLPY | 504.63 |
| 14 | VSPGAL | 542.29 |
| 15 | LAYPQ | 590.26 |
| 16 | TIFPQ | 604.31 |
| 17 | FIIPQ | 616.76 |
| 18 | LLPSSQ | 643.74 |

Comparative Embodiment 1

Take the corn oligopeptide powder obtained by the method disclosed in Chinese patent application No. 200810084992.5 as Comparative Embodiment 1, which method specifically includes:

Mix 2.5 kg of water with 150 g of corn protein powder into a slurry, adjust pH value to 8, heat to 60° C. and perform stirring in water bath at this temperature for 60 min, centrifuge the slurry and discard supernatant, dilute the resulting slag by adding 2.5 kg of water, heat to 60° C. and perform stirring in water bath at this temperature for 60 min, perform centrifugation and discard supernatant, add 2 kg of water for slurrying, adjust pH value to 8 and then heat to 60° C., add 1 g of alkaline protease for enzymolysis for 3 h, adjust pH value again to 7, lower the temperature to 45° C. and then add 1 g of neutral protease for enzymolysis for 5 h, perform centrifugal separation after deactivating enzyme at a high temperature, filter the resulting supernatant using a ceramic membrane and a rolled nanofiltration membrane, and perform concentration and drying to obtain a corn oligopeptide powder. Upon detection, the content of the oligopeptide with molecular weight of lower than 1000 Da in the corn oligopeptide powder is 80%, and the endotoxin content is more than 2000 EU/g.

Experimental Embodiment 1

1. Preparation of Serum-Free Culture Medium

Dissolve the corn active peptide obtained in Embodiments 1-3, the corn oligopeptide obtained in Comparative Embodiment 1, and MEWM/F12 (volume ratio is 1:1) culture medium respectively using pyrogen-free ultrapure water, to obtain peptide solutions and MEWM/F12 culture medium solution, they each having a concentration quadruple corresponding conventional concentration; mix the prepared peptide solutions respectively with the DMEM/F12 culture medium solution, and add ultrapure water to 95% of final volume, adjust pH value to 7.2-7.3 and dilute to the final volume, perform degerming by a 0.22 μb filter membrane, to obtain corresponding serum-free cultural mediums, wherein the corn active peptides obtained in Embodiments 1-3 and the corn oligopeptide obtained in Comparative Embodiment 1 each has a concentrations of 0.5 g/L in their respective serum-free culture medium when used for cell density detection, and each has a concentrations of 6 g/L or 10 g/L when used for antibody expression quantity detection. They are served as experimental groups 1-3 and comparative group, respectively; and meanwhile, take the DMEM/F12 culture medium without adding the corn active peptide as blank group.

2. Cell Culturing

Add culture mediums of the above experimental groups 1-3, comparative group and blank group respectively into a 2 L bioreactor, and inoculate CHO cells with activity of more than 95% into the bioreactor for suspension culturing, wherein the culturing conditions are: 37° C., and 5% of carbon dioxide; timing sampling and perform detections on cell density and antibody expression quantity using flow cytometry and reversed high performance liquid chromatography. The results are shown in FIG. 2 and FIG. 3.

Figure 2:
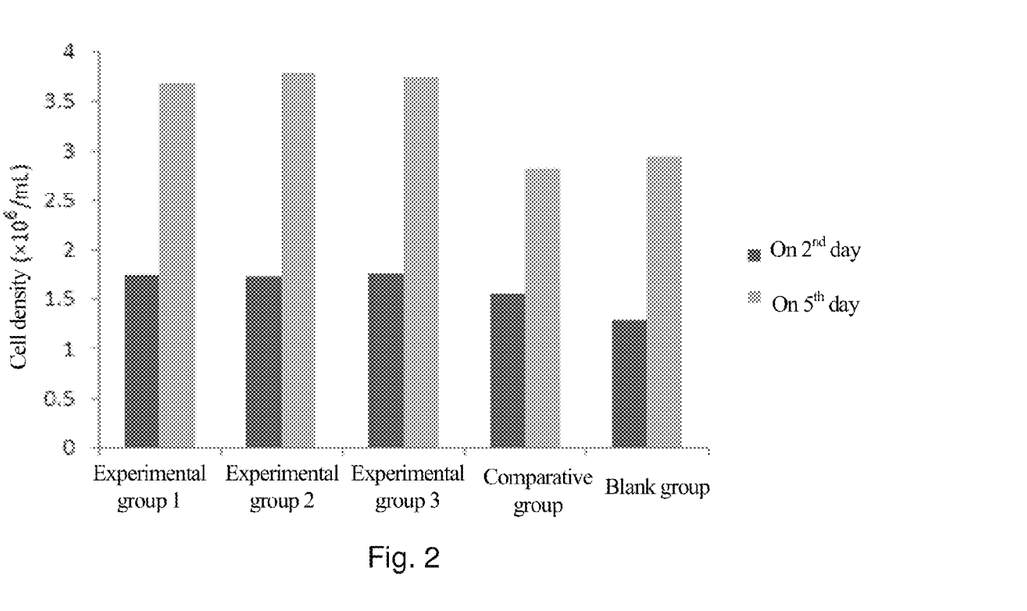
FIG. 2 is a diagram of cell density of the CHO cell cultured in Experimental Embodiment 1.
Figure 3:
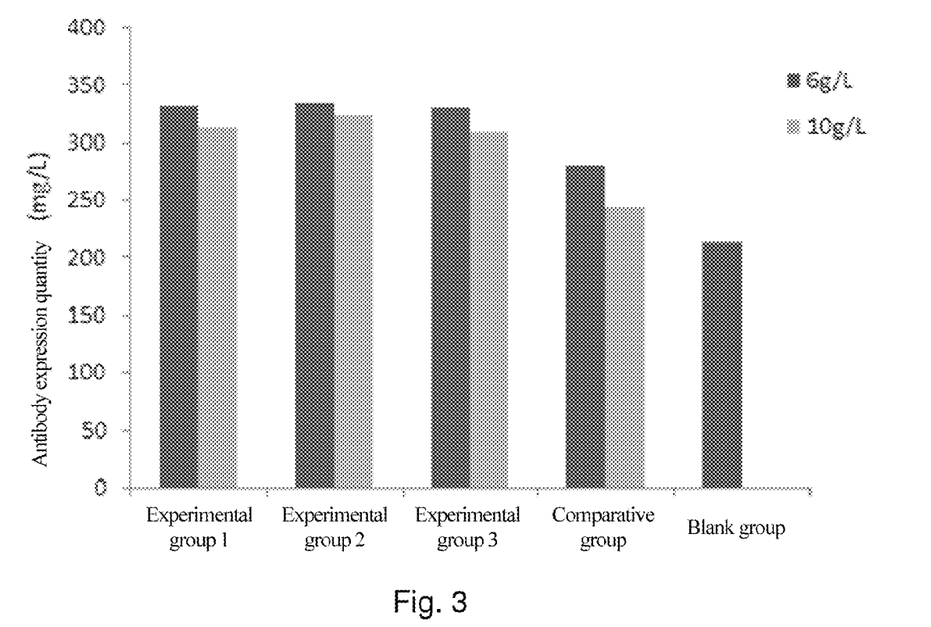
FIG. 3 is a diagram of antibody expression quantity of the CHO cell cultured in Experimental Embodiment 1.

As shown in FIG. 2, when the corn active peptides and the corn oligopeptide are added in an amount of 0.5 g/L, on the second day during culturing, cell densities in the culture medium of the experimental groups 1-3 are respectively 135%, 133%, and 135% of cell density in the culture medium of the blank group, and on the second and fifth days during culturing, cell density in the comparative group is respectively 120% and 96% of that in the blank group. As shown in FIG. 3, when the corn active peptides and the corn oligopeptide are added in an amount of 6 g/L, after culturing for six days, that is on the sixth day, cell antibody expression quantities in culture mediums of experimental groups 1-3 are respectively 154%, 156%, and 154% of cell antibody expression quantity in culture medium of the blank group, and when the corn active peptides and the corn oligopeptide are added in an amount of 10 g/L, cell antibody expression quantities in the culture mediums of experimental groups 1-3 are respectively 146%, 151%, and 144% of cell antibody expression quantity in the blank group, while cell antibody expression quantity in the culture medium of the comparative group, in the case of 6 g/L and 10 g/L, are respectively 131% and 113% of that in the blank group. It can be seen that: cells grow well when using the corn active peptides obtained by the Embodiments 1-3 as an additive of the cell culture medium, the corn active peptide can provide comprehensive nutrition for CHO cells, and part of the peptide also can be provided as functional factor for cell growth and metabolism, which is beneficial for promoting cell proliferation and enhance expression of cell products; in addition, the effect of the corn active peptide may be related to its concentration, 0.5 g/L is more suitable for the cell proliferation, where the concentration in the range of 6 g/L-10 g/L can significantly improve the antibody expression quantity. The present invention uses enzymatic hydrolysate of the corn protein to produce a cell culture medium additive, having a cost far below the cost when using serum, and such a culture medium additive is derived from plant, and thus has high safety.

Experimental Embodiment 2

1. Preparation of Serum-Free Culture Medium

Dissolve the corn active peptides obtained in Embodiments 1-3, the corn oligopeptide obtained in Comparative Embodiment 1 and IMDM culture medium respectively using pyrogen-free ultrapure water, to obtain peptide solutions and IMDM culture medium solution, they each having a concentrations quadruple corresponding conventional concentration; mix the prepared peptide solutions respectively with the IMDM culture medium solution, and add ultrapure water to 95% of final volume, adjust pH value to 7.2-7.3 and dilute to the final volume, perform degerming by a 0.22 μm filter membrane, to obtain corresponding serum-free cultural mediums, wherein the corn active peptides obtained in Embodiments 1-3 and the corn oligopeptide obtained in Comparative Embodiment 1 each has a concentrations of 4 g/L in their respective serum-free culture medium, which are served as experimental groups 1-3 and comparative group, respectively; and meanwhile, take the IMDM culture medium without adding the corn active peptide as blank group.

2. Cells Culturing

Add culture mediums of the above experimental groups 1-3, comparative group and blank group respectively into a shake flask, and inoculate CHO cells with good growth state into the shake flask for culturing, wherein the culturing conditions are: 37° C., and 5% of carbon dioxide; the speed of the shake flask is 100 rpm; timing sampling and perform detection on cell viability using flow cytometry AO/PI staining. The results are shown in FIG. 4.

Figure 4:
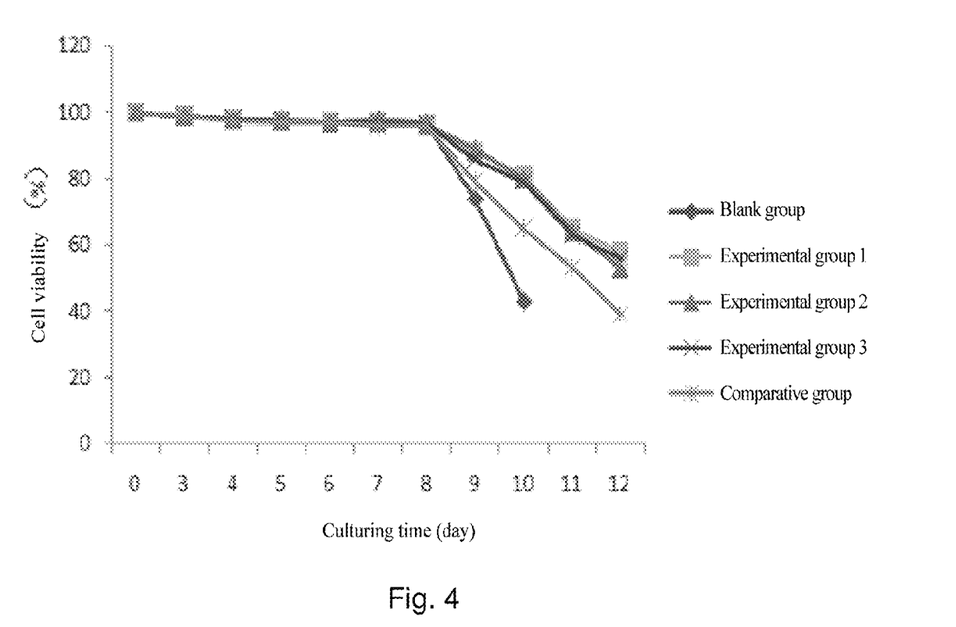
FIG. 4 is a diagram of cell viability of the CHO cell cultured in Experimental Embodiment 2.

As shown in FIG. 4, relative to the comparative group and the blank group, the culture mediums of the experimental groups 1-3 can obtain a higher cell viability within the same culturing time, and especially on the tenth day during culturing, the cell viabilities in the experimental groups 1-3 are respectively 81%, 80%, and 79%, the cell viability in the comparative group is 65% and the cell viability of the blank group is significantly reduced, only 43%. It can be seen that: the corn active peptides obtained by the Embodiments 1-3 of the present invention can provide comprehensive nutrition for CHO cells, and solve problems such as premature cell death and unsaturated cell morphology due to lacking of serum to some extent, thereby being beneficial for improving cell viability and enhancing expression of cell products.

Experimental Embodiment 3

1. Preparation of Serum-Free Culture Medium

Dissolve the corn active peptides obtained in embodiments 1-3, the corn oligopeptide obtained in Comparative Embodiment 1, and DMEM (high glucose) culture medium respectively using pyrogen-free ultrapure water, to obtain peptide solutions and DMEM culture medium solution, they each having a concentrations quadruple corresponding conventional concentration; mix the prepared peptide solutions respectively with the DMEM (high glucose) culture medium solution, and add ultrapure water to 95% of final volume, adjust pH value to 7.2-7.3 and dilute to the final volume, perform degerming by a 0.22 μm filter membrane, to obtain corresponding serum-free cultural mediums, wherein the corn active peptides obtained in Embodiments 1-3 and the corn oligopeptide obtained in Comparative Embodiment 1 each has a concentrations of 2 g/L in their respective serum-free culture medium, which are served as experimental groups 1-3 and comparative group, respectively; and meanwhile, take the DMEM (high glucose) culture medium without adding the corn active peptide as blank group.

2. Cells Culturing

Add culture mediums of the above experimental groups 1-3, comparative group and blank group respectively into a cell culture plate, and inoculate Africa green monkey kidney (Vero) cells with an activity of more than 95% into the cell culture plate for culturing, wherein the culturing conditions are: 37° C., and 5% of carbon dioxide; perform detection on cell density using MTT. The results are shown in FIG. 5.

Figure 5:
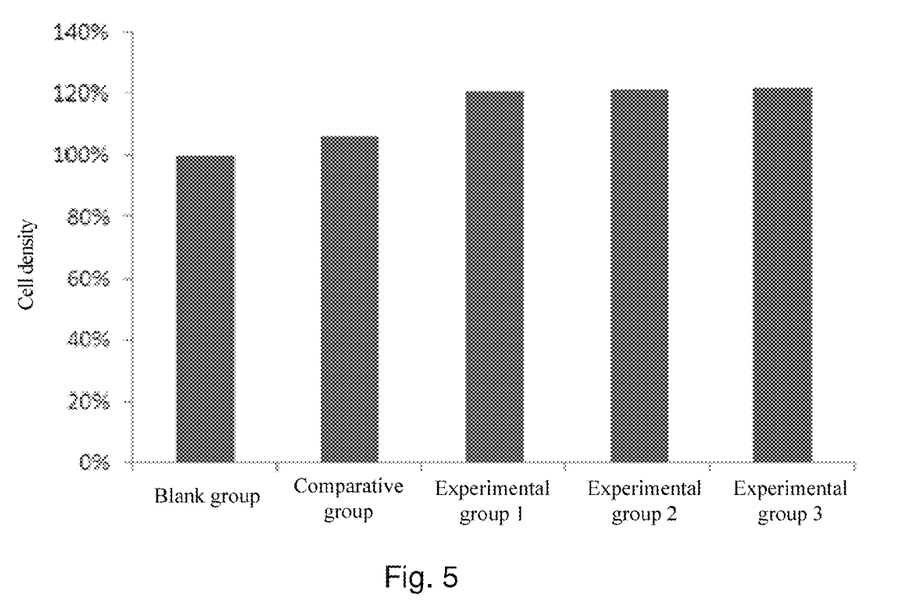
FIG. 5 is a diagram of cell density of the Vero cell cultured in Experimental Embodiment 3.

As shown in FIG. 5, the Vero cells of experimental groups 1-3 have rapid proliferation and vigorous metabolism, and the cell densities of experimental groups 1-3 are respectively 120.9%, 121.8%, and 122.3% of those of the blank group, and the Vero cell density of the comparative group is only 106.3% of that of the blank group, which indicates that using the culture medium with corn active peptide additive of the present invention for culturing the Vero cells can obtain a higher cell density within the same culturing time.

Experimental Embodiment 4

Dissolve the corn active peptides obtained in Embodiments 1-3, the corn oligopeptide obtained in Comparative Embodiment 1 and MEWM/F12 (volume ratio is 1:1) culture medium respectively using pyrogen-free ultrapure water, to obtain peptide solutions and MEWM/F12 culture medium solution, they each having a concentrations quadruple corresponding conventional concentration; mix the prepared peptide solutions respectively with the DMEM/F12 culture medium solution, add vitamin, fatty acid and microelement properly, and then add ultrapure water to 95% of final volume, adjust pH value to 7.2-7.3 and dilute to the final volume, perform degerming by a 0.22 μm filter membrane, to obtain corresponding serum-free cultural mediums, wherein the concentrations of the corn active peptides obtained in Embodiments 1-3 and the corn oligopeptide obtained in Comparative Embodiment 1 in their respective serum-free culture medium are all 5 g/L, which are served as experimental groups 1-3 and comparative group, respectively; and meanwhile, take the DMEM/F12 culture medium with addition of the same amount of vitamin, fatty acid and microelement as blank group.

Add culture mediums of the above experimental groups 1-3, comparative group and blank group respectively into a 2 L bioreactor, and inoculate hybridoma cells with an activity of more than 95% into the bioreactor for suspension culturing, wherein the culturing conditions are: 1 L of operation volume, dissolved oxygen is controlled at 50% of saturated air concentration, $2.5 \times 10^5$ cells/ml of inoculation density, 37° C., and 90 rpm of stirring speed; obtain an antibody after culturing for 6 days, and perform detection on the antibody expression quantity using ELISA method. The results are shown in FIG. 6.

Figure 6:
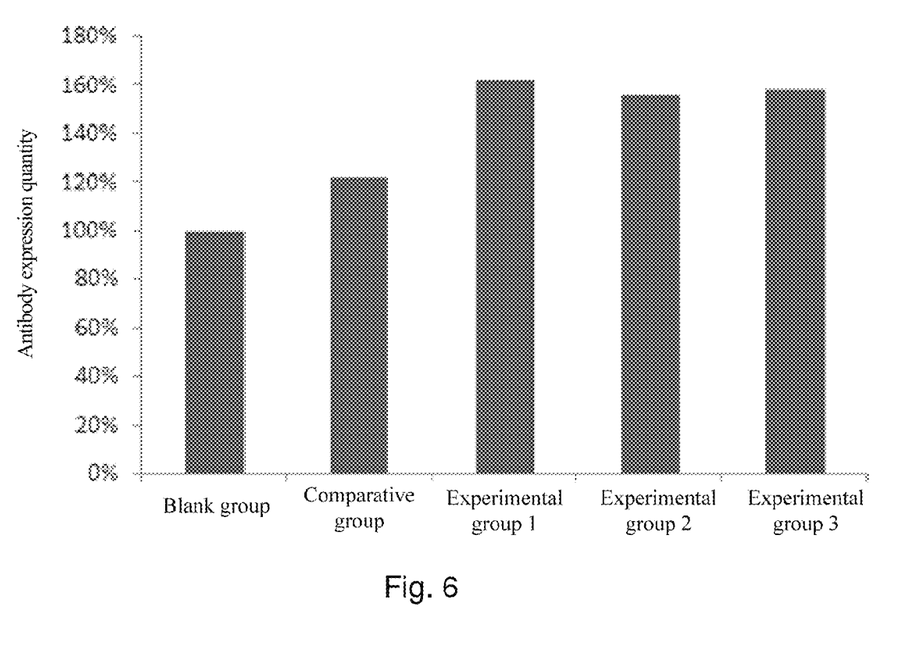
FIG. 6 is a diagram of antibody expression quantity of the hybridoma cell cultured in Experimental Embodiment 4.

As shown in FIG. 6, the antibody expression quantities in the experimental groups 1-3 are increased by respectively 62%, 56%, and 58% comparing with that in the blank group, and the antibody expression quantity in the comparative group is only increased by 22% comparing with that in the blank group, which indicates that using the culture medium with the corn active peptide additive of the present invention for culturing the hybridoma cells can obtain a higher antibody expression quantity within the same culturing time.

Experimental Embodiment 5

Dissolve the corn active peptides obtained in embodiments 1-3, the corn oligopeptide obtained in Comparative Embodiment 1 and MEM culture medium respectively using pyrogen-free ultrapure water, to obtain peptide solutions and MEM culture medium solution, they each having a with the resulting concentrations quadruple corresponding conventional concentrations; mix the prepared peptide solutions respectively with the MEM culture medium solution, add vitamin, fatty acid and microelement properly, and add ultrapure water to 95% of final volume, adjust pH value to 7.2-7.3 and dilute to the final volume, perform degerming by a 0.22 µm filter membrane, to obtain corresponding serum-free cultural mediums, wherein the corn active peptides obtained in Embodiments 1-3 and the corn oligopeptide obtained in Comparative Embodiment 1 each has a concentration of 7 g/L in their respective serum-free culture medium, which are served as experimental groups 1-3 and comparative group, respectively; and meanwhile, take the MEM culture medium with addition of the same amount of vitamin, fatty acid and microelement as blank group.

Add culture mediums of the above experimental groups 1-3, comparative group and blank group respectively into a 2 L bioreactor, and inoculate HEK-293 cells with an activity of more than 95% into the bioreactor for suspension culturing, wherein the culturing conditions are: 1 L of operation volume, dissolved oxygen is controlled at 50% of saturated air concentration, $2.0\times10^5$ cells/ml of inoculation density, 37° C., and 80 rpm of stirring speed; timing sampling and perform detection on cell viability using AO/PI staining. The results are shown in FIG. 7.

Figure 7:
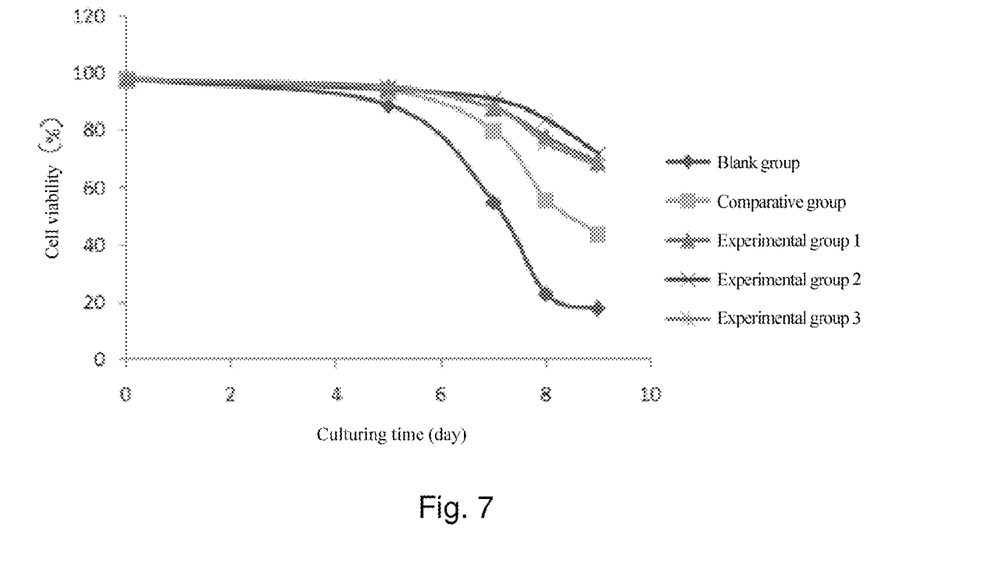
FIG. 7 is a diagram of cell viability of the HEK-293 cell cultured in Experimental Embodiment 5.

As shown in FIG. 7, relative to the comparative group and the blank group, the HEK-293 cells cultured in culture mediums of the experimental groups 1-3 have a higher cell viability within the same culturing time, which indicates that the corn active peptide additive of the present invention can significantly improve the cell viability of the HEJ-293 cells.

Experimental Embodiment 6

Dissolve the corn active peptides obtained in Embodiments 1-3, the corn oligopeptide obtained in Comparative Embodiment 1 and DMEM (less sugar) culture medium respectively using pyrogen-free ultrapure water, to obtain peptide solutions and DMEM culture medium solution, they each having a concentration quadruple corresponding conventional concentration; mix the prepared peptide solutions respectively with the DMEM (less sugar) culture medium solution, add vitamin, fatty acid and microelement properly, and add ultrapure water to 95% of final volume, adjust pH value to 7.0-7.2 and dilute to the final volume, perform degerming by a 0.22 µm filter membrane, to obtain corresponding serum-free cultural mediums, wherein the corn active peptides obtained in Embodiments 1-3 and the corn oligopeptide obtained in Comparative Embodiment 1 each has a concentration of 3 g/L in their respective serum-free culture medium, which are served as experimental groups 1-3 and comparative group, respectively; and meanwhile, take the DMEM (less sugar) culture medium with addition of the same amount of vitamin, fatty acid and microelement as blank group.

Add culture mediums of the above experimental groups 1-3, comparative group and blank group respectively into a 150 ml shake flask, and inoculate BHK-21 cells with an activity of more than 95% into the shake flask for suspension culturing, wherein the culturing conditions are: 40 mL of operation volume, $3.0\times10^5$ cells/ml of inoculation density, 37° C., and 100 rpm of stiffing speed; timing sampling and perform detection on cell density using a cell counter. The results are shown in FIG. 8.

Figure 8:
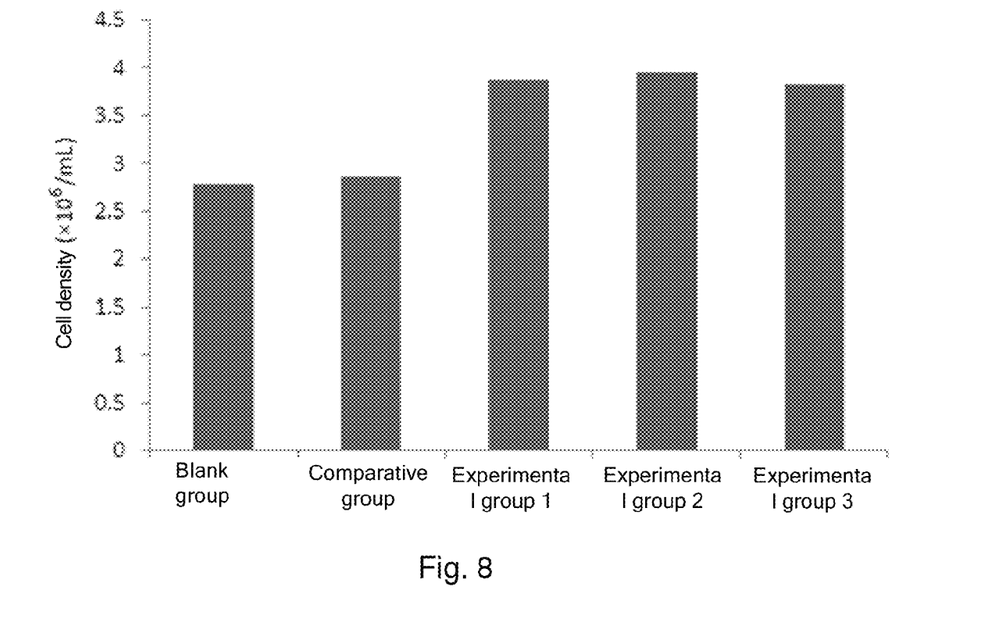
FIG. 8 is a diagram of cell density of the BHK-21 cell cultured in Experimental Embodiment 6.

As shown in FIG. 8, the cell densities of the experimental groups 1-3 are respectively 138%, 141%, and 136% of the cell density of the blank group, and the cell density of the comparative group is only 103% of that of the blank group, which indicates that when using the culture medium with the corn active peptide additive of the present invention for culturing the BHK-21 cell can increase their cell densities significantly within the same culturing time and promote their proliferation.

Experimental Embodiment 7

Dissolve the corn active peptides obtained in embodiments 1-3, the corn oligopeptide obtained in Comparative Embodiment 1 and MEM culture medium respectively using pyrogen-free ultrapure water, to obtain peptide solutions and MEM culture medium solution, they each having a concentration quadruple corresponding conventional concentration; mix the prepared peptide solutions respectively with the MEM culture medium solution, add vitamin, fatty acid and microelement properly, and add ultrapure water to 95% of final volume, adjust pH value to 7.0-7.2 and dilute to the final volume, perform degerming by a 0.22 µm filter membrane, to obtain corresponding serum-free cultural mediums, wherein the corn active peptides obtained in embodiments 1-3 and the corn oligopeptide obtained in Comparative Embodiment 1 each has a concentration of 6.5 g/L in their respective serum-free culture medium, which are served as experimental groups 1-3 and comparative group, respectively; and meanwhile, take the MEM culture medium with addition of the same amount of vitamin, fatty acid and microelement as blank group.

Add culture mediums of the above experimental groups 1-3, comparative group and blank group respectively into a 2 L bioreactor, and inoculate MARC-145 cells with an activity of more than 95% into the bioreactor for suspension culturing, wherein the culturing conditions are: 1 L of operation volume, $2.0\times10^5$ cells/ml of inoculation density, dissolved oxygen is controlled at 50% of saturated air concentration, 37° C., and 80 rpm of stirring speed; timing sampling and perform detection on cell density using a cell counter. The results are shown in FIG. 9.

Figure 9:
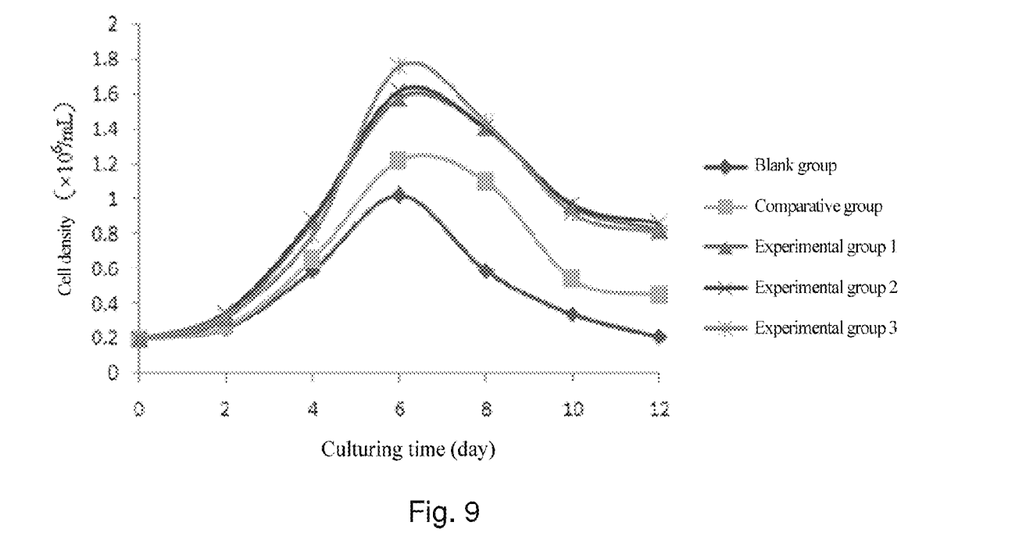
FIG. 9 is a diagram of cell density of the MARC-145 cell cultured in Experimental Embodiment 7.

As shown in FIG. 9, the MARC-145 cells cultured in culture mediums of experimental groups 1-3 have higher cell densities within the same culturing time, which indicates that the corn active peptide additive of the present invention is beneficial for promoting proliferation of the MARC-145 cells.

Experimental Embodiment 8

Dissolve the corn active peptides obtained in embodiments 1-3, the corn oligopeptide obtained in Comparative Embodiment 1 and DMEM (high glucose) culture medium respectively using pyrogen-free ultrapure water, to obtain peptide solutions and DMEM culture medium solution, they each having a concentration quadruple corresponding conventional concentration; mix the prepared peptide solutions respectively with the MEM culture medium solution, add vitamin, fatty acid and microelement properly, and add ultrapure water to 95% of final volume, adjust pH value to 7.0-7.2 and dilute to the final volume, perform degerming by a 0.22 µm filter membrane, to obtain corresponding serum-free cultural mediums, wherein the corn active peptides obtained in embodiments 1-3 and the corn oligopeptide obtained in Comparative Embodiment 1 each has a concentration of 2.5 g/L in their respective serum-free culture medium, which are served as experimental groups 1-3 and comparative group, respectively; and meanwhile, take the DMEM (high glucose) culture medium with addition of the same amount of vitamin, fatty acid and microelement as blank group.

Add culture mediums of the above experimental groups 1-3, comparative group and blank group respectively into a 150 ml shake flask, and inoculate MDCK cells with an activity of more than 95% into the shake flask for suspension culturing, wherein the culturing conditions are: 40 mL of operation volume, $3.0\times10^5$ cells/ml of inoculation density, 37° C., and 100 rpm of stirring speed; timing sampling and perform detection on cell viability using AO/PI staining. The results are shown in FIG. 10.

Figure 10:
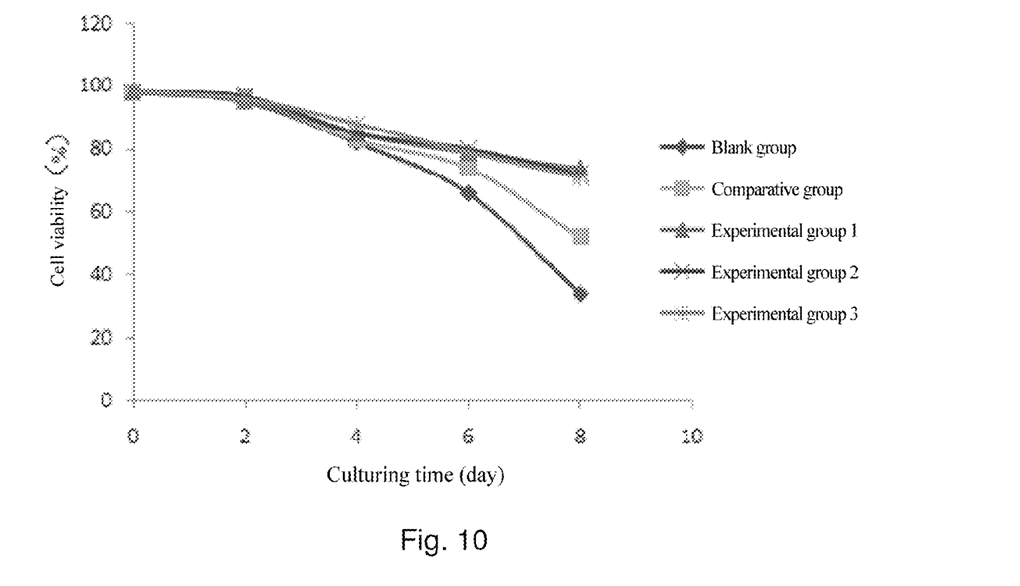
FIG. 10 is a diagram of cell viability of the MDCK cell cultured in Experimental Embodiment 8.

As shown in FIG. 10, relative to the comparative group and the blank group, the MDCK cells cultured in culture medium of experimental groups 1-3 have a higher cell viability within the same culturing time, which indicates that the corn active peptide additive of the present invention can improve the cell viability of the MDCK cells significantly.

It should be noted that, the above embodiments are only for describing the technical solutions of the present invention, but not for limiting. Although the present invention has been described in detail with reference to the foregoing embodiments, a person skilled in the art should understand: modifications to the technical solutions disclosed in the foregoing embodiments or equivalent replacements of part or all of the technical features in these embodiments can also be made, and these modifications or replacements will not make the essences of corresponding technical solutions depart from the scope of the technical solutions of the embodiments of the present invention.

What is claimed is:

1. A corn active peptide additive for cell culture medium, wherein in the corn active peptide additive, oligopeptides with molecular weight of lower than 1000 Dalton account for equal to or more than 90 wt % of total proteins, and the oligopeptides at least comprise a mixture, the mixture comprises AP, AY, SAP, IP, SEQ ID No.6, SEQ ID No.8 and SEQ ID No.9.

2. The corn active peptide additive according to claim 1, wherein endotoxin content in the corn active peptide additive is less than 200 EU/g.

3. The corn active peptide additive according to claim 1, wherein the corn active peptide additive is obtained by performing enzymolysis on corn gluten meal using a non-specific protease and a specific protease in sequence and then performing separation and purification.

4. The corn active peptide additive according to claim 3, wherein the non-specific protease is selected from one or more of papain, alkaline protease, neutral protease and bromelain, and the specific protease is selected from one or two of carboxypeptidase and flavourzyme.

5. A serum-free culture medium comprising the corn active peptide additive according to claim 1, wherein the corn active peptide additive has a concentration of 0.01-20 g/L in the serum-free culture medium.

6. A method of preparing the corn active peptide additive according to claim 1, comprising the following steps:
  1) performing a first enzymolysis process on the corn gluten meal using a non-specific protease to obtain a first enzymatic hydrolysate; and then performing a second enzymolysis process on the first enzymatic hydrolysate using a specific protease to obtain a corn protein enzymatic hydrolysate; and
  2) performing centrifugation on the corn protein enzymatic hydrolysate, and then performing microfiltration, cation exchange, nanofiltration and ultrafiltration in sequence on centrifugalized supernatant to obtain a corn active peptide; wherein the microfiltration is performed by a filter membrane with an aperture of 50-500 nm, the nanofiltration is performed by a filter membrane with molecular weight cut-off of 100-300 Dalton, and the ultrafiltration is performed by a filter membrane with molecular weight cut-off of 5000-13000 Dalton.

7. The method according to claim 6, wherein the non-specific protease has an enzyme level of 2000-6000 units per gram of protein, including two or more of papain with 0-1000 units, alkaline protease with 500-2000 units, neutral protease with 500-2000 units and bromelain with 0-1500 units; and the specific protease has an enzyme level of 2000-3000 units per gram of protein, including one or two of carboxypeptidase with 500-2000 units and flavourzyme with 1000-2000 units.

8. The method according to claim 7, wherein the step 1) specifically comprises: mixing the corn gluten meal with water to obtain a protein solution, and then adding the non-specific protease into the protein solution to reach an enzyme level of 2000-6000 units per gram of protein, and performing the first enzymolysis process at 40-60° C. for 1.5-4.5 hours, to obtain the first enzymatic hydrolysate; and then adding the specific protease into the first enzymatic hydrolysate to reach an enzyme level of 2000-3000 units per gram of protein, performing the second enzymolysis process at 40-60° C. for 2-3 hours, and sterilizing to obtain the corn protein enzymatic hydrolysate.

9. The method according to claim 6, wherein the microfiltration in step 2) specifically comprises: performing a first microfiltration on the centrifugalized supernatant using a filter membrane with an aperture of 200-500 nm to obtain a first microfiltrate, and then performing a second microfiltration on the first microfiltrate using a filter membrane with an aperture of 50-200 nm to obtain a second microfiltrate.

10. The method according to claim 6, wherein the nanofiltration in step 2) specifically comprises: concentrating the centrifugalized supernatant after cation exchange to protein content being 5-10% using a rolled membrane with molecular weight cut-off of 100-300 Dalton, and then washing and filtering to make the washed and filtered centrifugalized supernatant has an inorganic salt content of less than or equal to 5%; and then concentrating the washed and filtered centrifugalized supernatant to protein content being 20-40%.

* * * * *

SEQUENCE LISTING

```
<160> NUMBER OF SEQ ID NOS: 11

<210> SEQ ID NO 1
<211> LENGTH: 4
<212> TYPE: PRT
<213> ORGANISM: Zea mays

<400> SEQUENCE: 1

Val Asn Ala Pro
1

<210> SEQ ID NO 2
<211> LENGTH: 4
<212> TYPE: PRT
<213> ORGANISM: Zea mays

<400> SEQUENCE: 2

Pro Ser Ser Gln
1

<210> SEQ ID NO 3
<211> LENGTH: 4
<212> TYPE: PRT
<213> ORGANISM: Zea mays

<400> SEQUENCE: 3

Pro Val Ile Asn
1

<210> SEQ ID NO 4
<211> LENGTH: 4
<212> TYPE: PRT
<213> ORGANISM: Zea mays

<400> SEQUENCE: 4

Ala Tyr Pro Gln
1

<210> SEQ ID NO 5
<211> LENGTH: 6
<212> TYPE: PRT
<213> ORGANISM: Zea mays

<400> SEQUENCE: 5

Thr Gln Pro Gly Pro Gln
1               5

<210> SEQ ID NO 6
```

```
<211> LENGTH: 4
<212> TYPE: PRT
<213> ORGANISM: Zea mays

<400> SEQUENCE: 6

Leu Leu Pro Tyr
1

<210> SEQ ID NO 7
<211> LENGTH: 6
<212> TYPE: PRT
<213> ORGANISM: Zea mays

<400> SEQUENCE: 7

Val Ser Pro Gly Ala Leu
1               5

<210> SEQ ID NO 8
<211> LENGTH: 5
<212> TYPE: PRT
<213> ORGANISM: Zea mays

<400> SEQUENCE: 8

Leu Ala Tyr Pro Gln
1               5

<210> SEQ ID NO 9
<211> LENGTH: 5
<212> TYPE: PRT
<213> ORGANISM: Zea mays

<400> SEQUENCE: 9

Thr Ile Phe Pro Gln
1               5

<210> SEQ ID NO 10
<211> LENGTH: 5
<212> TYPE: PRT
<213> ORGANISM: Zea mays

<400> SEQUENCE: 10

Phe Ile Ile Pro Gln
1               5

<210> SEQ ID NO 11
<211> LENGTH: 6
<212> TYPE: PRT
<213> ORGANISM: Zea mays

<400> SEQUENCE: 11

Leu Leu Pro Ser Ser Gln
1               5
```